US012672885B2

(12) United States Patent
King et al.

(10) Patent No.: US 12,672,885 B2
(45) Date of Patent: Jul. 7, 2026

(54) QUICK-CONNECT K-WIRE MODULE

(71) Applicant: Phasor Health, LLC, Houston, TX (US)

(72) Inventors: Ray King, Houston, TX (US); Cody Bays, Pierceton, IN (US)

( * ) Notice: Subject to any disclaimer, the term of this patent is extended or adjusted under 35 U.S.C. 154(b) by 0 days.

(21) Appl. No.: 18/711,581

(22) PCT Filed: Nov. 18, 2022

(86) PCT No.: PCT/US2022/080111
§ 371 (c)(1),
(2) Date: May 18, 2024

(87) PCT Pub. No.: WO2023/092056
PCT Pub. Date: May 25, 2023

(65) Prior Publication Data
US 2025/0009362 A1     Jan. 9, 2025

Related U.S. Application Data

(60) Provisional application No. 63/280,914, filed on Nov. 18, 2021.

(51) Int. Cl.
*A61B 17/16*          (2006.01)
(52) U.S. Cl.
CPC ...... *A61B 17/1697* (2013.01); *A61B 17/1615* (2013.01); *A61B 17/162* (2013.01)
(58) Field of Classification Search
CPC . A61B 17/16; A61B 17/1613; A61B 17/1615; A61B 17/1617; A61B 17/162;
(Continued)

(56) References Cited

U.S. PATENT DOCUMENTS 5,794,715 A * 8/1998 Norman ............. A61B 17/1633
                                                      173/171
5,902,306 A * 5/1999 Norman ............. A61B 17/1697
                                                      606/104

(Continued)

*Primary Examiner* — Eric S Gibson
(74) *Attorney, Agent, or Firm* — Equip LG; Christopher Quan

(57) ABSTRACT

The present invention relates generally to a K-wire driver, particularly to a K-wire driver that interfaces with a drill equipped with a quick-connect mechanism, such as a surgical drill, and more particularly to a K-wire driver that is adapted to interface with a drill equipped with a quick-connect mechanism, such as a surgical drill, without changing modules on the drill or using a dedicated K-wire driver (i.e. with the same shaped interface engaging with the quick-connect for the K-wire as for the drill bit). Utilizing a K-wire mechanism with a quick-connect, with associated stabilization and concentricity, is desirable so that the same driver (e.g. surgical drill) with the quick-connect mechanism which can accommodate drill bits may likewise accommodate K-wire drivers of the present invention without removal of the quick-connect mechanism or module (the latter of which is required in all known present such models which interchangeably accommodate K-wire drivers vs. drilling), hence precluding the complexity (and need for reuse/re-sterilization) and associated cost of disposing what is typically a reused K-wire module/drill assembly.

14 Claims, 2 Drawing Sheets

(58) Field of Classification Search
CPC ............ A61B 17/1622; A61B 17/1624; A61B
17/1626; A61B 17/1628; A61B 17/1655;
A61B 17/1657; A61B 17/1697
See application file for complete search history.

(56) References Cited

U.S. PATENT DOCUMENTS

| | | | | | |
|---|---|---|---|---|---|
| 5,993,454 | A | * | 11/1999 | Longo | B23Q 5/048 |
| | | | | | 606/85 |
| 6,042,585 | A | * | 3/2000 | Norman | A61B 17/1697 |
| | | | | | 606/103 |
| 9,447,803 | B1 | * | 9/2016 | Fu | A61B 17/8875 |
| 9,458,890 | B1 | * | 10/2016 | Fu | F16D 1/108 |
| 9,532,789 | B2 | * | 1/2017 | Coope | A61B 17/1662 |
| 9,554,812 | B2 | * | 1/2017 | Inkpen | G01B 7/003 |
| 9,615,835 | B2 | * | 4/2017 | Lam | A61B 17/8685 |
| 10,993,729 | B1 | * | 5/2021 | Aman | A61B 17/1697 |
| 12,262,926 | B2 | * | 4/2025 | Jeffords | A61B 17/7082 |
| 2008/0097436 | A1 | * | 4/2008 | Culbert | A61B 17/7064 |
| | | | | | 606/103 |
| 2011/0054537 | A1 | * | 3/2011 | Miller | A61B 17/88 |
| | | | | | 606/279 |
| 2014/0148808 | A1 | * | 5/2014 | Inkpen | A61B 90/06 |
| | | | | | 73/866.5 |
| 2014/0276890 | A1 | * | 9/2014 | Khosla | A61B 17/162 |
| | | | | | 606/103 |
| 2015/0038970 | A1 | * | 2/2015 | Coope | A61B 17/1697 |
| | | | | | 606/80 |
| 2015/0297245 | A1 | * | 10/2015 | Lam | A61B 17/844 |
| | | | | | 408/127 |
| 2015/0351820 | A1 | * | 12/2015 | Straslicka | A61B 17/1697 |
| | | | | | 606/169 |
| 2017/0049460 | A1 | * | 2/2017 | Coope | A61B 17/1624 |
| 2017/0164953 | A1 | * | 6/2017 | Lam | A61B 17/8685 |
| 2019/0201009 | A1 | * | 7/2019 | Reed | A61B 17/1615 |
| 2020/0275967 | A1 | * | 9/2020 | Loftus-Vergari | B23B 31/1215 |
| 2020/0276689 | A1 | * | 9/2020 | Loftus-Vergari | B25B 23/0035 |
| 2021/0204964 | A1 | * | 7/2021 | Pather | B25G 3/24 |
| 2025/0009362 | A1 | * | 1/2025 | King | A61B 17/1615 |

* cited by examiner

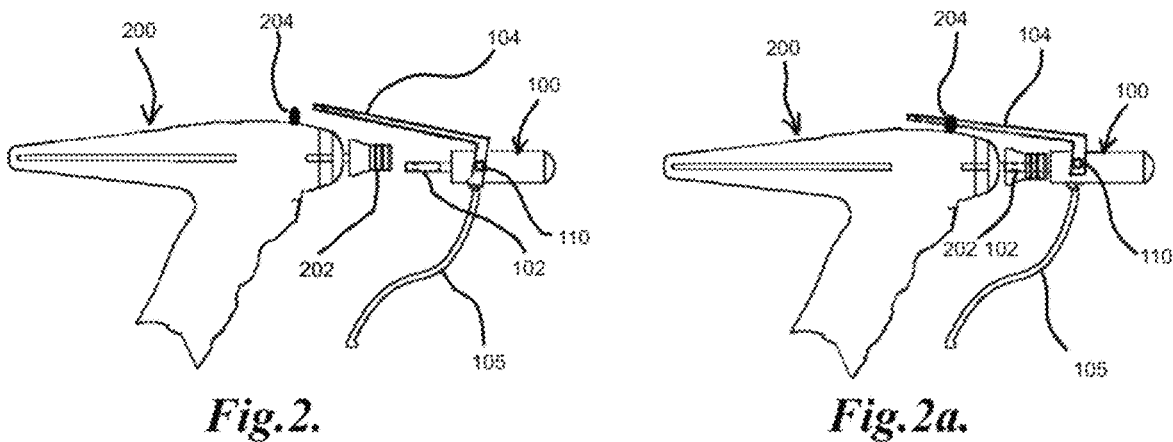
*Fig.2.*                                    *Fig.2a.*
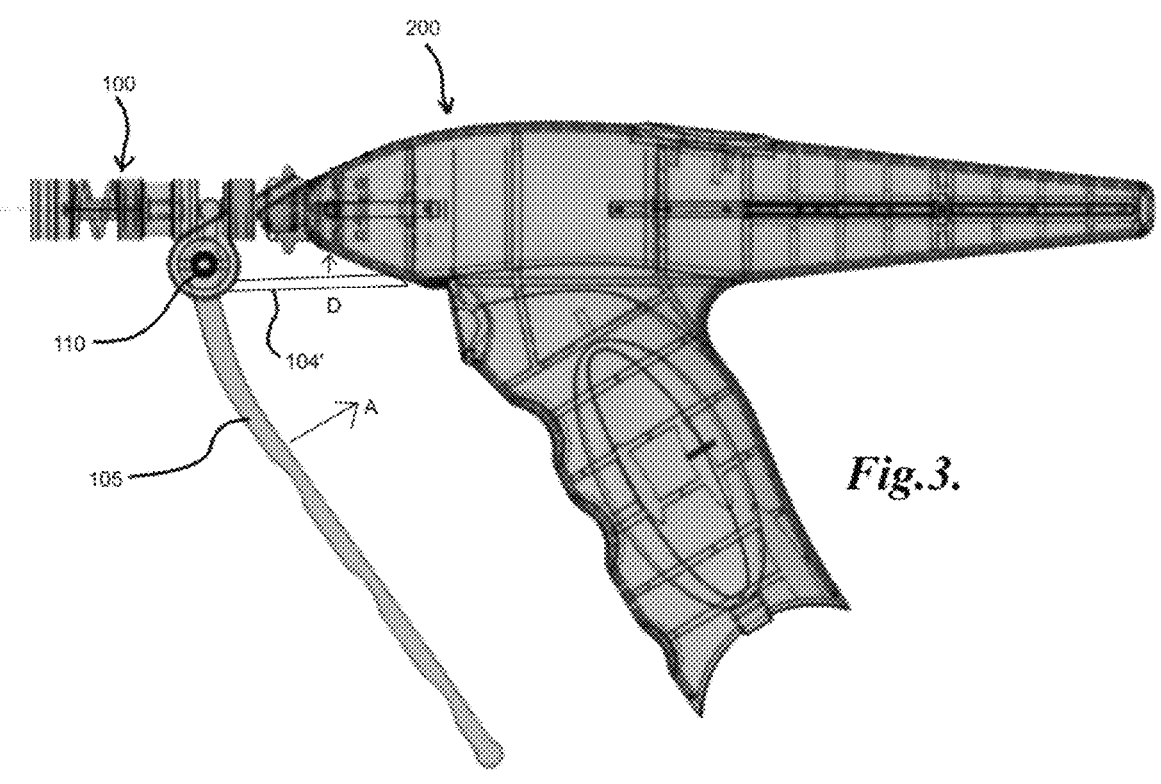
*Fig.3.*

QUICK-CONNECT K-WIRE MODULE

CROSS-REFERENCE TO RELATED APPLICATIONS

This application claims the benefit and priority of U.S. provisional patent application Ser. No. 63/280,914, filed Nov. 18, 2021, the contents of which is hereby incorporated by reference in its entirety.

FIELD OF THE INVENTION

The present invention relates generally to a K-wire driver, particularly to a K-wire driver that interfaces with a drill equipped with a quick-connect mechanism, such as a surgical drill, and more particularly to a K-wire driver that is adapted to interface with a drill equipped with the same quick-connect mechanism that presently interfaces with drills, such as a surgical drill, without changing modules on the drill or using a separate dedicated K-wire driver.

BACKGROUND OF THE INVENTION

It is often desirable to drill using various medical devices, e.g. for cranial, orthopedic, and other types of procedures. Current drills are available in varieties, including power sourced via batteries (disposable or reusable, single-use vs. rechargeable), pneumatic, electrical via cord connection to a wall outlet, etc.; drill bits themselves are engaged in varieties into such drills (either connected permanently to the motors or other internal mechanism, be capable of being engaged or disengaged via a chuck or chuckless system, or allow quick-connect interchangeability, e.g. via snapping in/out or having male/female connection with a peel-back or push-forward sleeve and spring-loaded mechanism).

K-wires or Kirschner wires are typically metal wires with a sharpened or driving tip that are driven into bone, utilizing drivers "K-wire drivers" which presently are intrinsic to the drill mechanism itself, or utilize a module which connects into the drill itself. No known K-wire driver mechanism presently connects via a quick-connect mechanism utilizing the same interface as for the drill bit, e.g. an Association for Osteosynthesis (AO)-style quick connect interface (or simply referred to as an AO quick-connect), which can simply be connected to the drill similar to a drill bit e.g. utilizing a male end of the K-wire driver (as for a drill bit) which fits into the female quick-connect portion on the drill itself.

SUMMARY OF THE INVENTION

The present invention relates generally to a K-wire driver, particularly to a K-wire driver that interfaces with a drill equipped with a quick-connect mechanism, such as a surgical drill, and more particularly to a K-wire driver that is adapted to interface with a drill equipped with a quick-connect mechanism, such as a surgical drill, without changing modules on the drill or using a dedicated K-wire driver. Utilizing a K-wire mechanism with a quick-connect, with associated stabilization and concentricity, is desirable so that the same driver (e.g. surgical drill) with the quick-connect mechanism which can accommodate drill bits may likewise accommodate K-wire drivers of the present invention without removal of the quick-connect mechanism or module (the latter of which is required in all known present such models which interchangeably accommodate K-wire drivers vs. drilling).

In one aspect of the invention, a system for K-wire placement may generally include a driver device (e.g. a drill or more particularly a surgical drill) that may include a quick-connect mechanism (e.g. an AO quick-connect) for interfacing with a tool (e.g. a drill bit) which may interface with a K-wire driver device of the present invention via such quick-connect mechanism without changing components or modules. In general, the quick-connect mechanism of the driver may include a female end of the quick-connect interface, but drivers with a male end may also be utilized. The appropriate interfacing end of the quick-connect interface may then be provided on the K-wire driver device to interface with the driver. In some embodiments, the quick-connect mechanism of the driver may generally include a chuck for adjustability for different sized tools. In other embodiments, a chuckless system may be utilized.

In another aspect of the invention, the system for K-wire placement may utilize a K-wire driver device, as mentioned above, with a quick-connect interface that is complementary to the interface of the driver and a mechanism for manipulating or articulating a K-wire or similar wire or tool to, for example, drill or drive into a tissue to enter and/or secure itself in the tissue. In general, the driver may utilize rotational driving to drill into the tissue with the sharp or tool end of the K-wire or other tool. By utilizing the step of simply removing a drill bit, connecting the K-wire driver device via the same quick-connect mechanism, and then proceeding with K-wire driving, the additional step typically required in such drills of removing a module and fitting a K-wire driver in a method other than contemplated here, is negated; moreover, a separate dedicated K-wire driver is not needed.

In a further aspect of the invention, the K-wire driver device may include an actuation mechanism that reversibly grasps the K-wire during driving and releases it when driving is stopped or completed. In some embodiments, the K-wire may be retained in a channel of the body of the K-wire driver device, and may include features in the channel that grip the K-wire (e.g. through frictional or compressional engagement), such as through tapered grooves in the lumen of the channel with the lumen being radially compressed by pushing forward into a tapering section, such as with an actuating mechanism. The K-wire driver device may further include a mechanism for releasing the grip, such as, for example, by radially decompressing the channel via releasing the actuating mechanism which may, for example, widen the lumen of the channel to cause the gripping features to disengage from the K-wire. The actuating mechanism may further include a return feature, such as a return spring or other appropriate feature, which may reset the lumen of the channel when the actuation mechanism is released. In some embodiments, an opposite arrangement may be utilized where the actuation mechanism decompresses the lumen to release the grip on the K-wire and releasing the actuation mechanism compresses the lumen to grip the K-wire.

In yet another aspect of the invention, the K-wire driver device may include features for stabilizing the interface with the driver. In general, interfaced components may experience flex or other deformation during use, such as from driving forces or from actuation of grips, triggers, etc. In some embodiments, a stabilizer may be included on the K-driver device to engage with a portion of the driver separate from the quick-connect interface to provide a separate leveraged point of stabilization. For example, a hook or other engagement may latch onto or push up against a portion of the driver housing. The driver may further include a feature for such engagement which may be integral to the driver or may be a separate piece that may be attached for use with the K-wire driver device. The stabilizer may also be adjustable, movable and/or lockable relative to the remainder of the K-wire driver device for fitting, retaining and/or removal from the driver.

The present invention together with the above and other advantages may best be understood from the following detailed description of the embodiments of the invention and as illustrated in the drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE FIGURES

FIGS. 2 and 2a illustrate the attachment of a K-wire driver device to a driver via a quick-connect mechanism and stabilization features; and FIG. 3 illustrates an alternative stabilization feature.

DETAILED DESCRIPTION OF THE INVENTION

Figures 1, 1A:
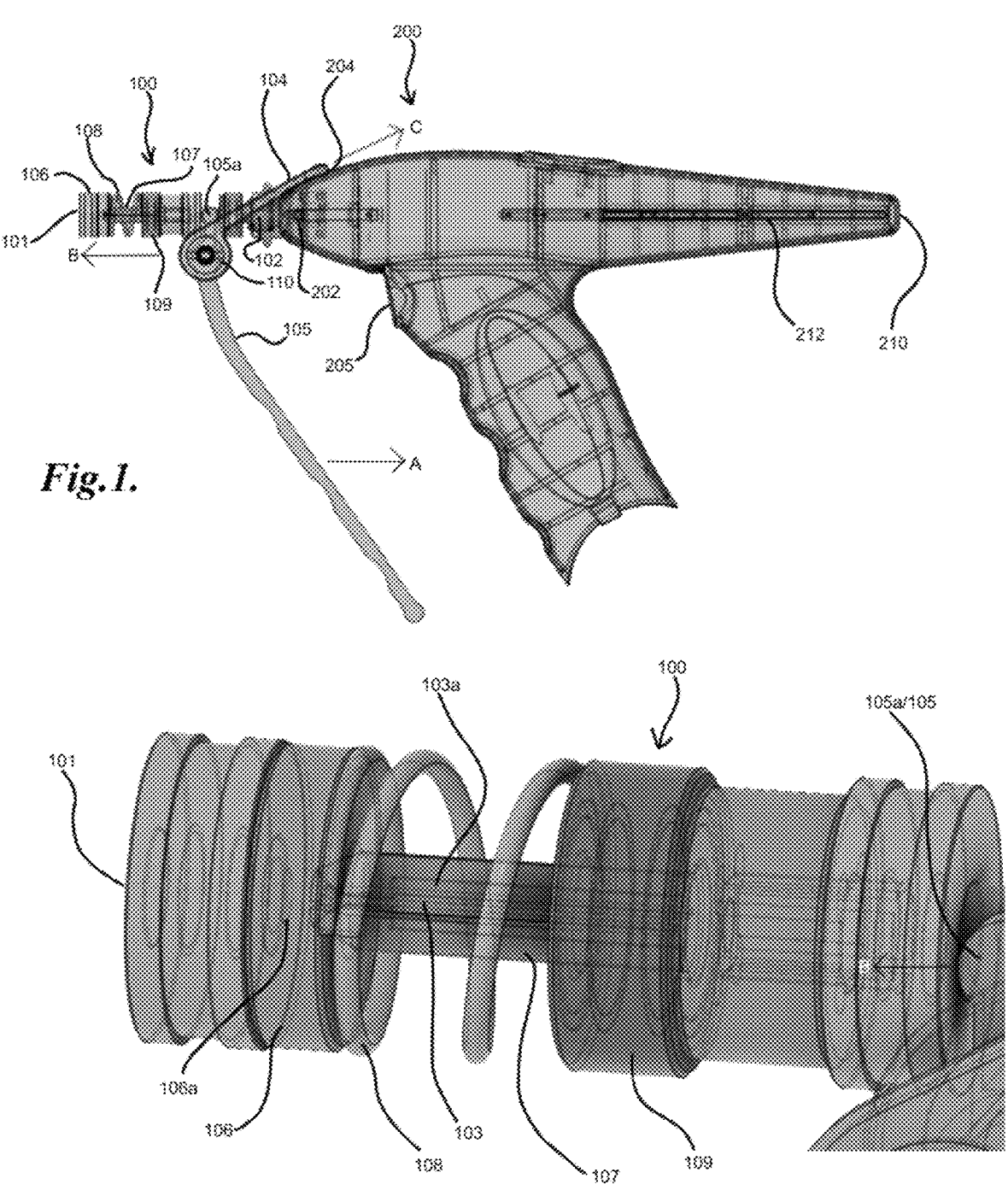
FIG. 1 illustrates an embodiment of the system of the present invention, with a driver and K-wire driver device attached via a quick-connect mechanism.
FIG. 1a illustrates a partial see-through view of a K-wire driver device showing a retention and actuation features.

The detailed description set forth below is intended as a description of the presently exemplified systems, devices and methods provided in accordance with aspects of the present invention and are not intended to represent the only forms in which the present invention may be prepared or utilized. It is to be understood, rather, that the same or equivalent functions and components may be accomplished by different embodiments that are also intended to be encompassed within the spirit and scope of the invention. Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplary methods, devices and materials are now described. All publications mentioned herein are incorporated herein by reference for the purpose of describing and disclosing, for example, the designs and methodologies that are described in the publications which might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

The present invention relates generally to a K-wire driver, particularly to a K-wire driver that interfaces with a drill equipped with a quick-connect mechanism, such as a surgical drill, and more particularly to a K-wire driver that is adapted to interface with a drill equipped with a quick-connect mechanism, such as a surgical drill, without changing modules on the drill or using a dedicated K-wire driver—i.e. by fitting into the same location via a similar interface as an actual drill bit. Utilizing a K-wire mechanism with a quick-connect, with associated stabilization and concentricity, is desirable so that the same driver (e.g. surgical drill) with the quick-connect mechanism which can accommodate drill bits may likewise accommodate K-wire drivers of the present invention without removal of the quick-connect mechanism or module (the latter of which is required in all known present such models which interchangeably accommodate K-wire drivers vs. drilling). K-wires ranging from 0.5-mm to 2.0-mm, for treatment of small bone fractures, may be able to be driven using the existing power source (drill with a quick-connect mechanism already existing).

In one aspect of the invention, a system for K-wire placement may generally include a driver device (e.g. a drill or more particularly a surgical drill) that may include a quick-connect mechanism (e.g. an AO quick-connect) for interfacing with a tool (e.g. a drill bit) which may interface with a K-wire driver device of the present invention via such quick-connect mechanism without changing components or modules. In general, the quick-connect mechanism of the driver may include a female end of the quick-connect interface, but drivers with a male end may also be utilized. The appropriate interfacing end of the quick-connect interface may then be provided on the K-wire driver device to interface with the driver. In some embodiments, the quick-connect mechanism of the driver may generally include a chuck for adjustability for different sized tools. In other embodiments, a chuckless system may be utilized.

FIG. 1 illustrates an example of a driver 200 in the form of a surgical drill with a quick-connect interface 202, such as an AO quick-connect, for interfacing with a tool, such as a drill bit or a K-wire driver of this invention, and a trigger 205 for activating the driving. In general, this invention may be applied to disposable as well as reusable drills, of the varieties noted (pneumatic, electrical A/C current vs. battery-operated, using rechargeable vs. disposable batteries), or any other appropriate driver.

In another aspect of the invention, the system for K-wire placement may utilize a K-wire driver device, as mentioned above, with a quick-connect interface that is complementary to the interface of the driver and a mechanism for manipulating or articulating a K-wire or similar wire or tool to, for example, drill or drive into a tissue to enter and/or secure itself in the tissue. FIGS. 1 and 1a illustrate an embodiment of a K-wire driver device 100 which may include a quick-connect interface 102 which interfaces with the quick-connect interface 202 as illustrated. In general, the driver 200 may utilize rotational driving to drill into the tissue with the sharp or tool end of the K-wire or other tool. By utilizing the step of simply removing a drill bit, connecting the K-wire driver device 100 via the same quick-connect mechanism 202 of the driver 200, and then proceeding with K-wire driving, the additional step typically required in such drills of removing a module and fitting a K-wire driver in a method other than contemplated here, is negated; moreover, a separate dedicated K-wire driver is not needed.

In a further aspect of the invention, the K-wire driver device 100 may include an actuation mechanism that reversibly grasps the K-wire during driving and releases it when driving is stopped or completed. In some embodiments, the K-wire may be retained in a channel 107 of the body of the K-wire driver device 100, such as by insertion through aperture 101, and may include features in the channel 107 that grip the K-wire (e.g. through frictional or compressional engagement), such as through tapered grooves 103a in the lumen 103 of the channel 107 with the lumen 103 being radially compressed by pushing forward B into a tapering section 106a, such as in forward collet 106, such as with an actuating mechanism (e.g. the trigger 105 being pulled in direction A to cause actuator 105a to roll forward about rotational joint 110 to push on collet 109). The K-wire driver device 100 may further include a mechanism for releasing the grip, such as, for example, by radially decompressing the channel 107 via releasing the actuating mechanism which may, for example, widen the lumen 103 of the channel 107 to cause the gripping features 103a to disengage from the K-wire. The actuating mechanism may further include a return feature 108, such as a return spring or other appropriate feature, which may reset the lumen 103 of the channel 107 when the actuation mechanism is released, such as by pushing back against both collets 106, 109. In some embodiments, an opposite arrangement may be utilized where the actuation mechanism decompresses the lumen 103 to release the grip on the K-wire and releasing the actuation mechanism compresses the lumen 103 to grip the K-wire.

In yet another aspect of the invention, the K-wire driver device 100 may include features for stabilizing the interface with the driver 200. In general, interfaced components may experience flex or other deformation during use, such as from driving forces or from actuation of grips, triggers, etc. In some embodiments, a stabilizer may be included on the K-driver device 100 to engage with a portion of the driver 200 separate from the quick-connect interface (102, 202) to provide a separate leveraged point of stabilization. For example, a hook or other engagement may latch onto or push up against a portion of the driver housing, as illustrated with the stabilizer bar 104 interfacing at point 204 in FIG. 1. The driver 200 may further include a feature for such engagement which may be integral to the driver or may be a separate piece that may be attached (e.g. through adhesive, mechanical fastener or other appropriate method) for use with the K-wire driver device 100, such as a hook or other attachment point for the stabilizer bar 104 to attach, as shown with the attachment in FIGS. 2, 2a. The stabilizer may also be adjustable, movable and/or lockable relative to the remainder of the K-wire driver device 100 for fitting, retaining and/or removal from the driver 200. For example, as illustrated in FIGS. 1, 2, 2a, the stabilizer bar 104 may be able to rotate about the rotational joint 110 such as to, for example, adjust for different shaped/sized drivers, location of attachment points 204 or to aid in the attachment action. As illustrated in FIG. 1, the stabilizer bar 104 attaching provides a countering force C by providing tension against the action of the trigger 105 actuating in direction A to aid preventing flex about the quick-connect interface (102, 202). This is generally desirable as flex may result in altering of the desired trajectory of the K-wire during driving.

In other embodiments, such as illustrated in FIG. 3, a stabilizer bar 104' may be provided that presses up against the housing of the driver 200 in direction D in response to the trigger 105 acting direction A and may generally aid in resisting flex by more virtue of its rigidity rather than in more of a tensional arrangement in FIG. 1. This may be desirable in some situations where the driver 200 does not have an attachment point 204 or it is undesirable to attach one.

Example of a K-Wire Quick-Connect Mechanism in Conjunction with an Existing Drill being Used for Orthopedic Fracture Repair A complex fracture of the upper extremity, for example, may require multiple bones to be aligned and fixed, in a combination of drilling for open reduction and internal fixation (ORIF) and K-wire alignment of smaller bones (e.g.

bones of the hand). In such an instance, a drill utilized with a quick-connect mechanism would use the drill bits quickly interchanged via this connection, and thereafter the K-wire driver may be connected immediately, and K-wires placed through bones upon restoration of alignment, for such maintenance of alignment. This procedure could also allow versatility in the emergency room or other procedure room, as requiring operating room each time (which adds time delay, additional cost, and inconvenience at unusual hours post-traumatic injury. The K-wire driver being capable of further allowing wires of diameter 0.5-mm to 2.0-mm enables such alignment and driving through varying size bones as well, with added convenience of not requiring switching the K-wire driver(s). This would allow both easier one-time sterilization, disposability, use, and convenience of the entire drill with such K-wire attachments, whereas more complex modules may require more complex methods for re-sterilization for reutilization, and with complexity the price may prohibit disposability (which is needed to help reduce infection risk, as utilizing a new drill each time is still theoretically safer in patient-to-patient transmission than a reusable, re-sterilizable drill which is partly reused because of cost and complexity of the associated K-wire module.

Although the invention has been described with respect to specific embodiments thereof, these embodiments are merely illustrative, and not restrictive of the invention. The description herein of illustrated embodiments of the invention, including the description in the Abstract and Summary, is not intended to be exhaustive or to limit the invention to the precise forms disclosed herein. Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

Reference throughout this specification to "one embodiment", "an embodiment", or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention. As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, process, article, or apparatus.

The invention claimed is:

1. A method for placing a K-wire in a tissue comprising:
providing a driver comprising:
  a driver quick-connect interface at a front end of said driver; and
  a drill bit with a corresponding quick-connect interface attached to said driver quick-connect interface;
performing a drilling operation with said driver;
removing said drill bit;
replacing said drill bit with a K-wire driver device comprising:
  a K-wire driver quick-connect interface that corresponds to said driver quick-connect interface;
  a K-wire retaining mechanism adapted to reversibly grip a K-wire in a channel upon actuation by an actuation mechanism; and
  a stabilizing feature for interfacing with said driver at a separate point from said driver quick-connect interface, said stabilizing feature comprising a stabilizer bar extending rearward of said K-wire driver device toward said front end of said driver and abutting a portion of said driver to counter flexing at said driver quick-connect interface;
inserting a K-wire into said channel;
actuating said actuation mechanism;
driving said K-wire via said K-wire driver device and driver; and
releasing said actuation mechanism to release said K-wire from said channel.

2. The method of claim 1, further comprising interfacing said stabilizer bar with an attachment point on said driver.

3. The method of claim 2, wherein said countering flexing comprises providing a countering force by providing tension between said K-wire driver device and said driver against said actuating of said actuation mechanism.

4. The method of claim 1, wherein a lumen in said channel is compressed to grip said K-wire when said actuation mechanism is actuated and decompressed when released to ungrip said K-wire.

5. The method of claim 1, wherein said driver quick-connect interface and said K-wire driver quick-connect interface comprise an AO quick-connect.

6. The method of claim 1, wherein said countering flexing comprises pushing up against said driver to oppose flexing from said actuating of said actuation mechanism by its rigidity.

7. The method of claim 1, wherein said stabilizer bar is attached to a rotational joint adapted to permit rotation of said stabilizer bar to adjust positioning.

8. A system for stereotactic placement of a catheter into a body cavity comprising:
  a driver comprising a driver quick-connect interface at a front end;
  a K-wire driver device disposed forward of and coupled to said driver comprising:
    a K-wire driver quick-connect interface that corresponds to said driver quick-connect interface;
    a K-wire retaining mechanism adapted to reversibly grip a K-wire in a channel upon actuation by an actuation mechanism; and
    a stabilizing feature for interfacing with said driver at a separate point from said driver quick-connect interface comprising a stabilizer bar extending rearward of said K-wire driver device toward said driver and adapted to abut a portion of said driver to counter flexing at said driver quick-connect interface.

9. The system of claim 8, wherein said stabilizing feature further comprises an attachment point on said driver adapted to interface with said stabilizer bar.

10. The system of claim 9, wherein said stabilizer bar is adapted to provide a countering force by providing tension between said K-wire driver drive and said driver against said actuation mechanism.

11. The system of claim 8, further comprising a lumen in said channel adapted to grip said K-wire by compressing in response to said actuation mechanism in an actuated state and adapted to degrip said K-wire by decompressing said actuation mechanism in a de-actuated state.

12. The system of claim 8, wherein said driver quick-connect interface and said K-wire driver quick-connect interface comprise an AO quick-connect.

13. The system of claim 8, wherein said stabilizer bar is adapted to push against said driver to oppose flexing from said actuation mechanism by its rigidity.

14. The system of claim 8, wherein said stabilizer bar is attached to a rotational joint adapted to permit rotation of said stabilizer bar to adjust positioning.

* * * * *